US010385300B2

(12) United States Patent
Iga et al.

(10) Patent No.: US 10,385,300 B2
(45) Date of Patent: Aug. 20, 2019

(54) CELL ANALYSIS APPARATUS AND METHOD

(71) Applicant: OLYMPUS CORPORATION, Tokyo (JP)

(72) Inventors: Yasunobu Iga, Tokyo (JP); Yohei Tanikawa, Tokyo (JP); Shinichi Takimoto, Tokyo (JP); Yoshinobu Akahori, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 56 days.

(21) Appl. No.: 15/653,967

(22) Filed: Jul. 19, 2017

(65) Prior Publication Data

US 2017/0313965 A1 Nov. 2, 2017

Related U.S. Application Data

(63) Continuation of application No. PCT/JP2015/052566, filed on Jan. 29, 2015.

(51) Int. Cl.
*G06K 9/00* (2006.01)
*C12M 1/34* (2006.01)
(Continued)

(52) U.S. Cl.
CPC .......... *C12M 1/3446* (2013.01); *C12M 41/46* (2013.01); *C12M 41/48* (2013.01); *G01N 21/8851* (2013.01); *G01N 2021/0143* (2013.01)

(58) Field of Classification Search
CPC ....... A61B 6/037; A61B 6/5235; A61B 6/585; G06T 7/0028; G06T 11/60; G06T 11/005;
(Continued)

(56) References Cited

U.S. PATENT DOCUMENTS

2007/0063142 A1 3/2007 Kanegasaki et al.
2013/0182936 A1* 7/2013 Yoshihara ............. G06T 7/0012
382/133

(Continued)

FOREIGN PATENT DOCUMENTS

JP S63-259465 A 10/1988
JP H02-269967 A 11/1990
(Continued)

OTHER PUBLICATIONS

International Search Report dated Apr. 21, 2015 issued in PCT/JP2015/052566.
(Continued)

*Primary Examiner* — Duy M Dang
(74) *Attorney, Agent, or Firm* — Scully, Scott, Murphy & Presser, P.C.

(57) ABSTRACT

A cell analysis apparatus including: a cell image acquisition unit that acquires an image of cells in a culture vessel in which cells are cultured; a smoothing processing unit that smooths luminance values in the image acquired by the cell image acquisition unit; a minimum-value detecting unit that detects minimum values of the luminance values smoothed by the smoothing processing unit; a smallest-minimum-value extracting unit that extracts smallest minimum values which are the smallest in regions according to the sizes of the cells, from the minimum values detected by the minimum-value detecting unit; a counting unit that counts the number of smallest minimum values extracted by the smallest-minimum-value extracting unit; and a cell-count calculating unit that calculates the number of cells in the culture vessel on the basis of the number of smallest minimum values counted by the counting unit.

12 Claims, 11 Drawing Sheets

(51) Int. Cl.
*G01N 21/88* (2006.01)
*C12M 1/36* (2006.01)
*G01N 21/01* (2006.01)

(58) Field of Classification Search
CPC ........ G06T 2207/30024; G06K 9/0014; G06K 9/00147; G06K 9/00127; G01N 15/1475
See application file for complete search history.

(56) References Cited

U.S. PATENT DOCUMENTS

| | | |
|---|---|---|
| 2013/0235066 A1 | 9/2013 | Souza |
| 2015/0262356 A1* | 9/2015 | Yoshihara ............. G06T 7/0012 382/133 |
| 2016/0025612 A1 | 1/2016 | Kuninori et al. |

FOREIGN PATENT DOCUMENTS

| | | |
|---|---|---|
| JP | 2007-048006 A | 2/2007 |
| JP | 2007-078614 A | 3/2007 |
| JP | 2010-246442 A | 11/2010 |
| JP | 2013-153714 A | 8/2013 |
| JP | 2014-082957 A | 5/2014 |

OTHER PUBLICATIONS

Chinese Office Action dated Apr. 29, 2019 received in Chinese Patent Application No. 201580074753.X, together with an English-language translation.

\* cited by examiner

CELL ANALYSIS APPARATUS AND METHOD

CROSS-REFERENCE TO RELATED APPLICATIONS

This is a continuation of International Application PCT/JP2015/052566 which is hereby incorporated by reference herein in its entirety.

TECHNICAL FIELD

The present invention relates to a cell analysis apparatus and method.

TECHNICAL FIELD

As a technique for counting the number of cells in a culture vessel, there is a technique in which the number of cells is counted using shape recognition of the cells from a phase contrast image (for example, see Patent Literature 1).

CITATION LIST

Patent Literature

{PTL 1}
Japanese Unexamined Patent Application, Publication No. 2007-78614

SUMMARY OF INVENTION

An aspect of the present invention is a cell analysis apparatus comprising: a cell image acquisition unit that acquires an image of cells in a culture vessel in which cells are cultured; a smoothing processing unit that smooths luminance values in the image acquired by the cell image acquisition unit; a minimum-value detecting unit that detects minimum values of the luminance values smoothed by the smoothing processing unit; a smallest-minimum-value extracting unit that extracts smallest minimum values which are the smallest in regions according to the sizes of the cells, from the minimum values detected by the minimum-value detecting unit; a counting unit that counts the number of smallest minimum values extracted by the smallest-minimum-value extracting unit; and a cell-count calculating unit that calculates the number of cells in the culture vessel on the basis of the number of smallest minimum values counted by the counting unit.

Another aspect of the present invention is a cell analysis apparatus comprising: a cell image acquisition unit that acquires an image of cells in a culture vessel in which cells are cultured; a smoothing processing unit that smooths luminance values in the image acquired by the cell image acquisition unit; a maximum-value detecting unit that detects maximum values of the luminance values smoothed by the smoothing processing unit; a largest-maximum-value extracting unit that extracts largest maximum values which are the largest in regions according to the sizes of the cells, from the maximum values detected by the maximum-value detecting unit; a counting unit that counts the number of largest maximum values extracted by the largest-maximum-value extracting unit; and a cell-count calculating unit that calculates the number of cells in the culture vessel on the basis of the number of largest maximum values counted by the counting unit.

Another aspect of the present invention is cell analyzing method comprising: an image-capturing step of acquiring an image of cells in a culture vessel in which the cells are cultured; a smoothing step of smoothing luminance values in the image acquired in the image-capturing step; a minimum-value detecting step of detecting minimum values of the luminance values smoothed in the smoothing step; a smallest-minimum-value extracting step of extracting smallest minimum values that are the smallest in regions according to the sizes of the cells, from the minimum values detected in the minimum-value detecting step; a counting step of counting the number of the smallest minimum values extracted in the smallest-minimum-value extracting step; and a cell-count calculating step of calculating the number of cells in the culture vessel on the basis of the number of smallest minimum values counted in the counting step.

Another aspect of the present invention is a cell analyzing method comprising: an image-capturing step of acquiring an image of cells in a culture vessel in which the cells are cultured; a smoothing step of smoothing luminance values in the image acquired in the image-capturing step; a maximum-value detecting step of detecting maximum values of the luminance values smoothed in the smoothing step; a largest-maximum-value extracting step of extracting largest maximum values that are the largest in regions according to the sizes of the cells, from the maximum values detected in the maximum-value detecting step; a counting step of counting the number of the largest maximum values extracted in the largest-maximum-value extracting step; and a cell-count calculating step of calculating the number of cells in the culture vessel on the basis of the number of largest maximum values counted in the counting step.

DESCRIPTION OF EMBODIMENTS

A cell analysis apparatus 1 according to an embodiment of the present invention will be described below with reference to the drawings.

Figure 1:
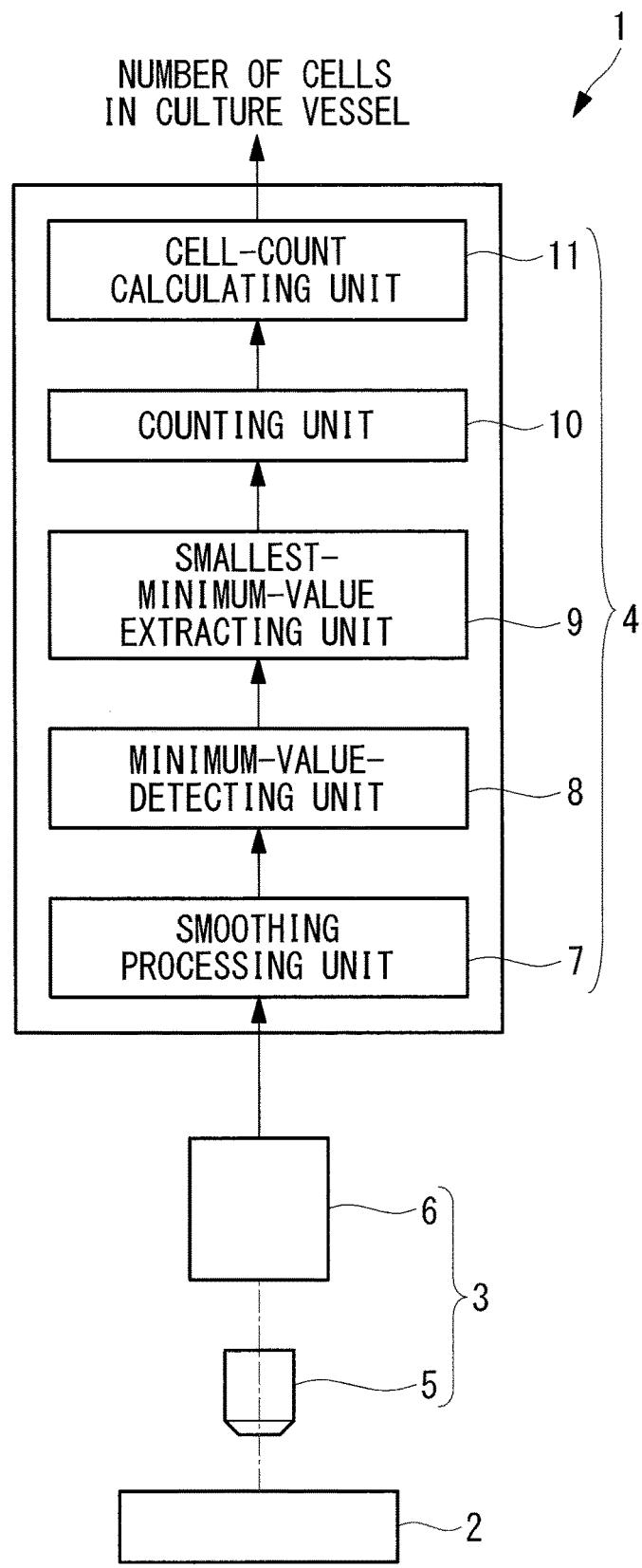
FIG. 1 is a diagram showing the overall configuration of a cell analysis apparatus according to an embodiment of the present invention.

As shown in FIG. 1, the cell analysis apparatus 1 according to this embodiment includes: a cell image acquisition unit 3 that acquires an image of cells A cultured in a culture vessel 2; and an image processing unit 4 that processes the image acquired by the cell image acquisition unit 3 and outputs the number of cells in the culture vessel 2.

The cell image acquisition unit 3 includes: an objective lens 5 that is disposed facing a culturing surface 2a of the culture vessel 2 culturing the cells A and that collects light from the culturing surface 2a; and a light detecting unit 6 that acquires an image covering a prescribed visual field in the culturing surface 2a by imaging the light collected by the objective lens 5.

As an image to be acquired, a phase-contrast image will be described as an example.

Figure 2:
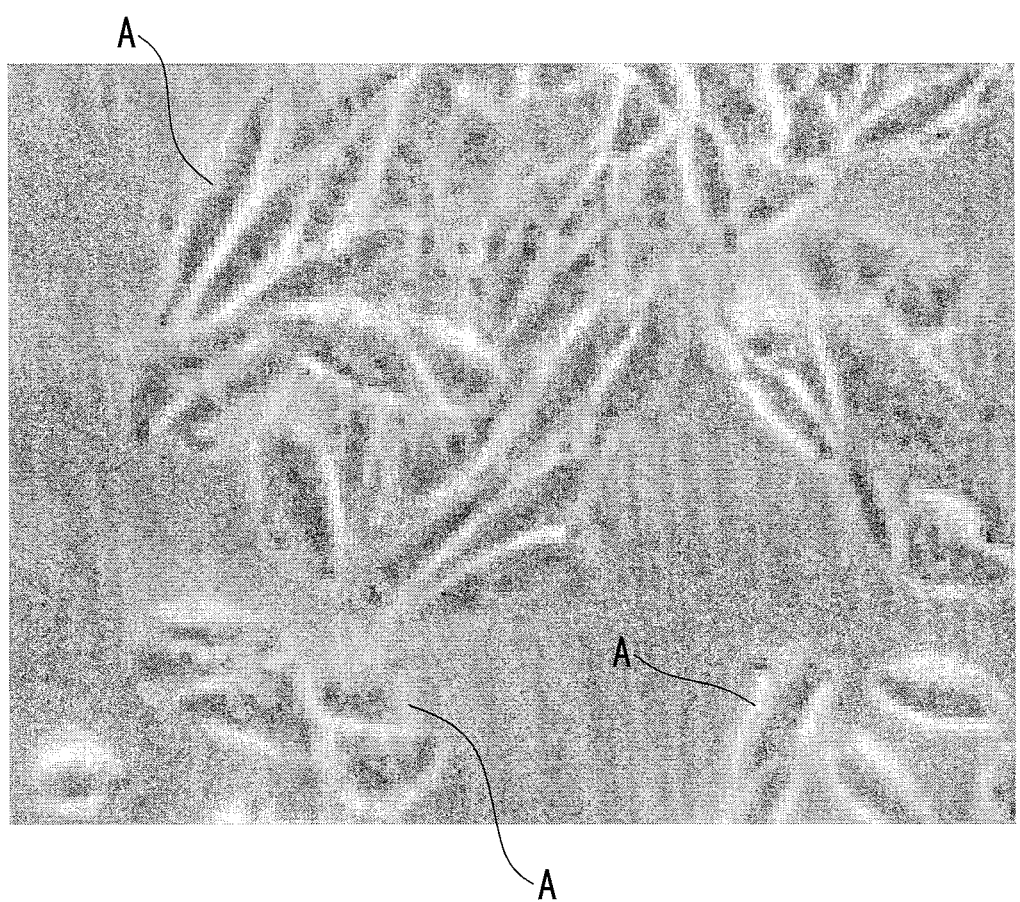
FIG. 2 is a diagram showing an example of an image of cells acquired by the cell analysis apparatus in FIG. 1.

An example of a phase-contrast image acquired by the cell image acquisition unit 3 is shown in FIG. 2.

According to this example, in the acquired image, cellular nuclei, cell organelles such as mitochondria or organelles that exist inside the cells appear as shadows, forming a plurality of black spots with lower luminance values (luminance value peaks).

The image processing unit 4 includes: a smoothing processing unit 7 that smooths the luminance values in the image of the cells A acquired by the light detecting unit 6; a minimum-value detecting unit that detects minimum values of the luminance values smoothed by the smoothing processing unit 7; a smallest-minimum-value extracting unit that extracts smallest minimum values from among the minimum values detected by the minimum-value detecting unit 8; a counting unit 10 that calculates the number of smallest minimum values extracted by the smallest-minimum-value extracting unit 9; and a cell-count calculating unit 11 that calculates the number of cells in the culture vessel 2 on the basis of the number of smallest minimum values counted by the counting unit 10.

The smoothing processing unit 7 is, for example, a low-pass filter, and removes high-frequency components from the image of the cells A, thereby softening the image. In other words, with the smoothing processing unit 7, by inputting a phase contrast image to the smoothing processing unit 7, the luminance values are smoothed so that the each luminance value peak becomes more gentle, and as for small-area luminance value peaks in particular, the peaks themselves become lower.

The minimum-value detecting unit 8 detects points where the luminance values are the minimum in the image smoothed by the smoothing processing unit 7. In this case, the minimum values that are smaller than the surrounding luminance values are detected, regardless of the size of the surface area.

The smallest-minimum-value extracting unit 9 extracts the minimum values that are the smallest within the region having the size of the cell A, from among the minimum values of the luminance values detected by the minimum-value detecting unit 8. Specifically, as shown in FIG. 3, in a region having luminance values less than or equal to luminance values obtained by adding a prescribed threshold value to the luminance values of the minimum values detected by the minimum-value detecting unit 8, the minimum values that are the smallest are extracted as the smallest minimum values.

Figure 3:
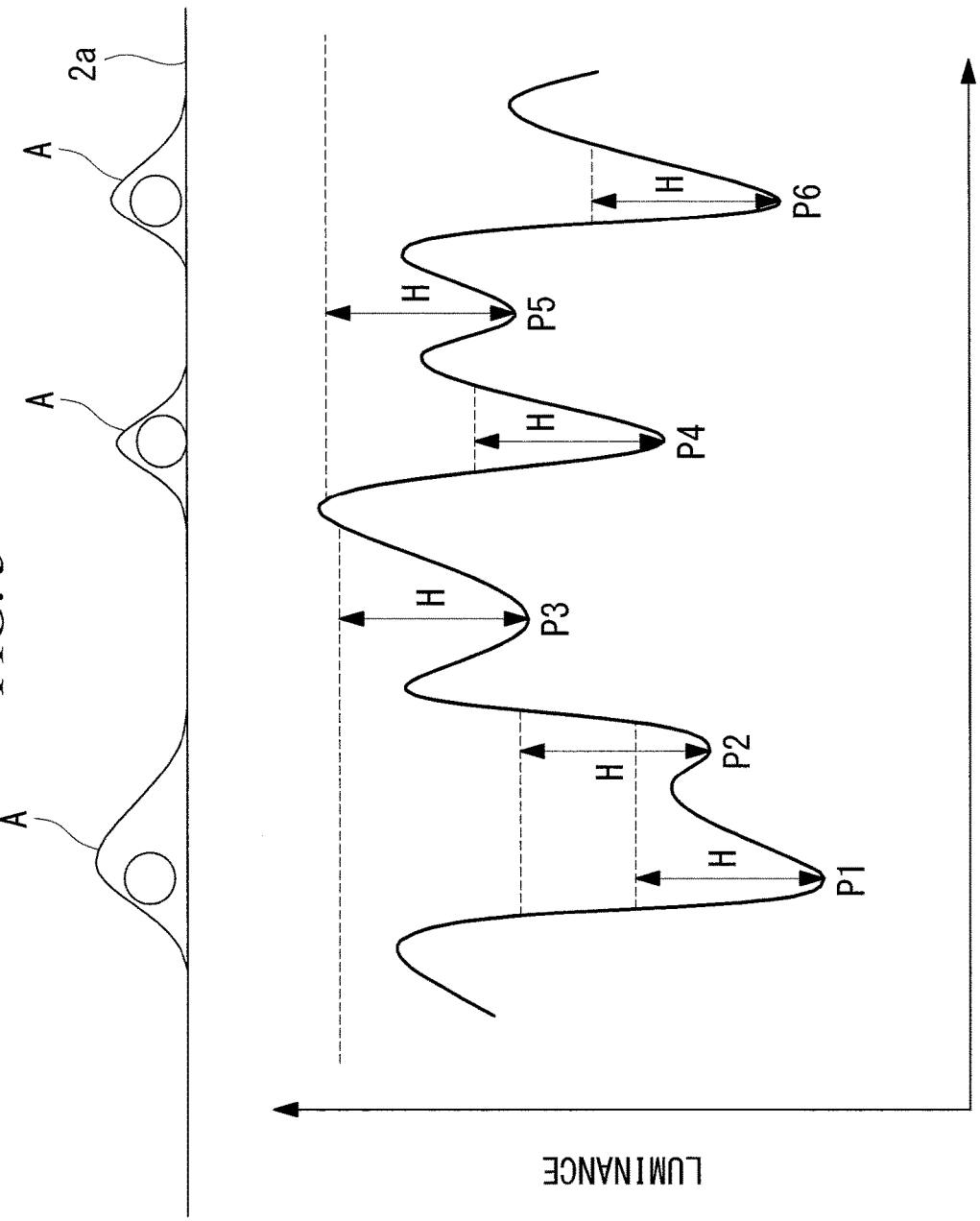
FIG. 3 is a diagram for explaining the operation of a smallest-minimum-value extracting unit in the cell analysis apparatus in FIG. 1.

In the example shown in FIG. 3, in the case where six minimum values P1 to P6 exist, first, at the minimum value P1, in a region containing the minimum value P1 and having luminance values less than or equal to a value obtained by adding a threshold value H to the luminance value of that minimum value P1, the minimum value P1, which is the smallest, is extracted as a smallest minimum value. Here, as the prescribed threshold H, an arbitrary constant that enables the region having luminance values less than or equal to a value obtained by adding the threshold value H to the luminance value of the minimum value to represent a region having the same size as the cell A is set in advance.

Next, at the minimum value P2 also, in a similar fashion, in a region containing the minimum value P2 and having luminance values less than or equal to a value obtained by adding the threshold H to the luminance value of the minimum value P2, the minimum value P1, which is the smallest, is extracted as the smallest minimum value, and the minimum value P2 is not extracted. The smallest-minimum-value extracting unit 9 performs the above-described processing on all of the minimum values.

The counting unit 10 counts the number of smallest minimum values extracted by the smallest-minimum-value extracting unit. Where multiple smallest minimum values are redundantly extracted by the smallest-minimum-value extracting unit 9, one is extracted as the smallest minimum value.

The cell-count calculating unit 11 multiplies the smallest minimum values counted by the counting unit 10 by the ratio of the effective area of the culturing surface 2a of the culture vessel 2 and the area of the visual field, thereby calculating the total number of cells in the culture vessel 2.

A cell analysis method using the thus-configured cell analysis apparatus 1 according to this embodiment will be described below.

Figure 4:
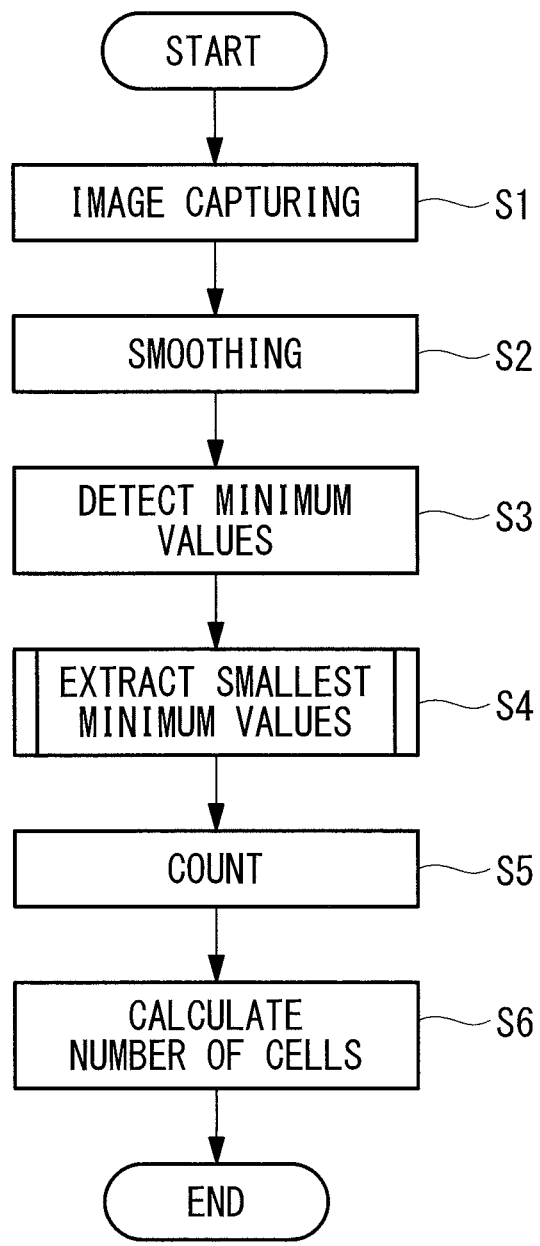
FIG. 4 is a flowchart showing a cell analysis method using the cell analysis apparatus in FIG. 1.

With the cell analysis method according to this embodiment, to calculate the number of cells in the culture vessel 2, first, as shown in FIG. 4, the objective lens 5 of the cell image acquisition unit 3 is disposed facing the culturing surface 2a of the culture vessel 2 in which the cells A are cultured, and the light from the culturing surface 2a, collected by the objective lens 5, is detected by the light detecting unit 6 to acquire an image (image-capturing step S1). By performing the image-capturing step S1, a phase contrast image of the cells A, shown in FIG. 2, is acquired.

Next, the luminance values of the image acquired in the image-capturing step S1 are smoothed in the smoothing processing unit 7 (smoothing step S2).

Figure 5:
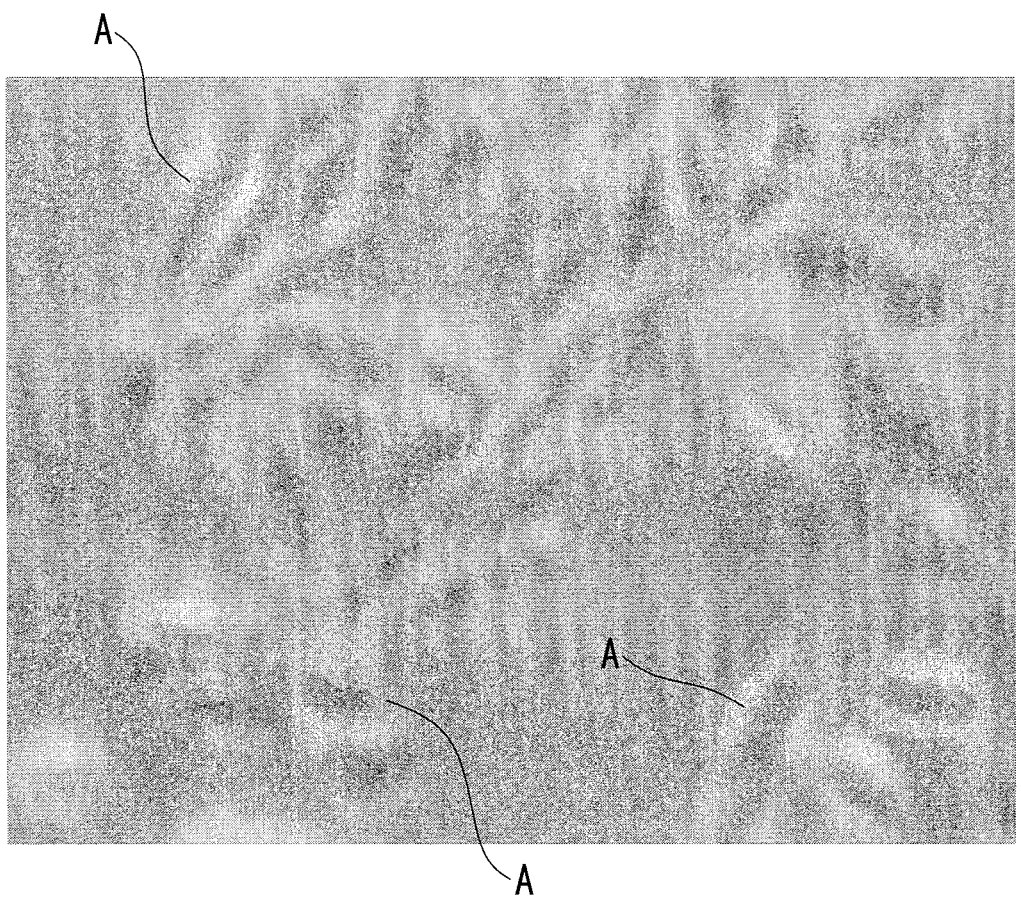
FIG. 5 is a diagram showing an example of an image of cells smoothed by a smoothing step in the cell analysis method in FIG. 4.

As shown in FIG. 5, a smoothed image in which the luminance values of the phase contrast image in FIG. 2 are softened is created in the smoothing step S2. In other words, in this smoothing step S2, the luminance values are smoothed to make the luminance value peaks more gentle, and in particular, for luminance value peaks in a small area, the peaks themselves become lower.

As a result, luminance value peaks of cellular nuclei, which are luminance value peaks having a large area, remain, and those luminance value peaks in regions of the same cells A therearound become the smallest minimum values.

In this state, the minimum values of the luminance values smoothed in the smoothing step S2 are detected by the minimum-value detecting unit 8 (minimum-value detecting step S3).

In the minimum-value detecting step S3, all of the minimum values existing in the image after the luminance values are smoothed are detected.

In other words, for the minimum values of the luminance values where the area was small, the luminance value peaks themselves become smaller in the smoothing step S3; however, in the minimum-value detecting step S3, in the example shown in FIG. 3, the minimum values P1 to P6, which are smaller than the surrounding luminance values, are detected.

Then, the smallest minimum values that are the smallest within the regions according to the sizes of the cells A are extracted, by the smallest-minimum-value extracting unit 9, from the minimum values detected in the minimum-value detecting step S3 (smallest-minimum-value extracting step S4). Accordingly, the smallest minimum values at which the luminance value at each cell A is the smallest are extracted.

Figure 6:
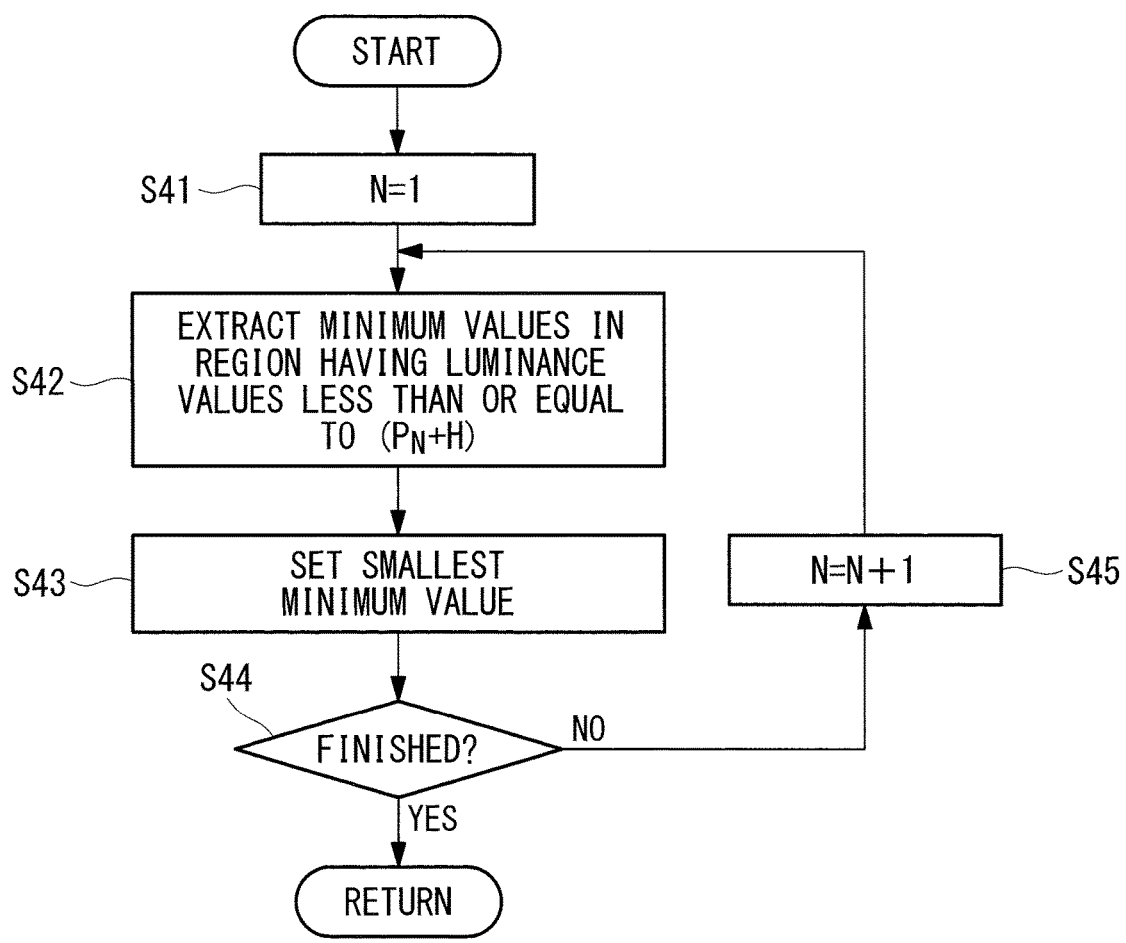
FIG. 6 is a flowchart showing a smallest-minimum-value extracting step in the cell analysis method in FIG. 4.

As shown in FIG. 6, in the smallest-minimum-value extracting step S4, after a number N is initialized (step S41), all of the minimum values existing within a continuous region containing the minimum value $P_N$ (N=1) and having luminance values less than or equal to a value obtained by adding the prescribed threshold value to that minimum value $P_N$ are extracted (step S42), and the smallest minimum value that is the smallest value among all of the extracted minimum values is set (step S43). This processing is repeated for all of the minimum values P1 to P6 (step S44).

Figure 7:
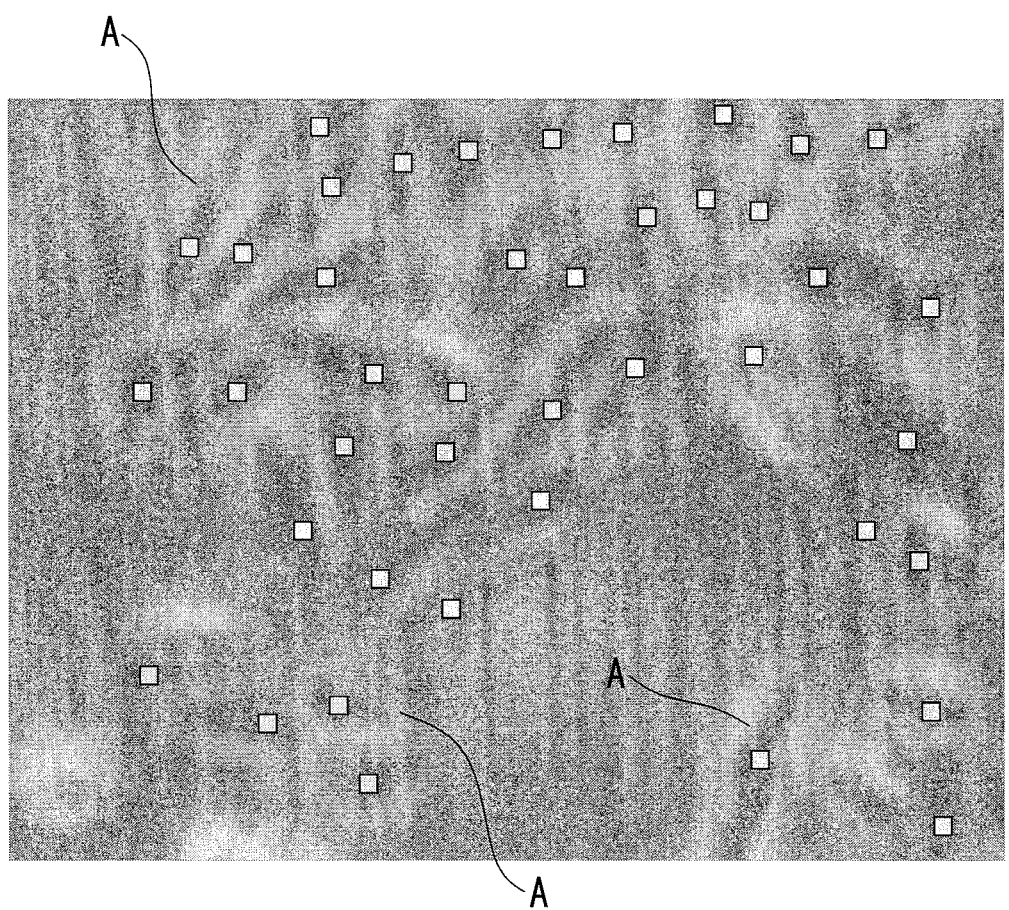
FIG. 7 is a diagram in which smallest minimum values extracted by the smallest-minimum-value extracting step in FIG. 6 are overlaid on the smoothed cell image in FIG. 5.

In other words, in the smoothing step S2, mainly the region of the cell nucleus, which is a region in each cell A where the luminance value in the largest area is low, is extracted in the smallest-minimum-value extracting step as the smallest minimum value where the luminance value is smaller than the other minimum values; therefore, as shown in FIG. 7, a single smallest minimum value (indicated by the marker in the figure) in each cell A can be extracted. In other words, the number of smallest minimum values is the number of cells.

Then, the number of smallest minimum values extracted in the smallest-minimum-value extracting step S4 is counted in the counting unit 10 (counting step S5). Accordingly, the number of cells in the image is counted.

Finally, the number of cells in the culture vessel 2 is calculated by the cell-count calculating unit 11 on the basis of the number of smallest minimum values counted in the counting step S5 (cell-count calculating step S6).

The visual field range based on the image acquired by the cell image acquisition unit 3 is predetermined, and the effective culturing area in which culturing of the cells A is substantially carried out on the culturing surface 2a of the culture vessels is also predetermined; therefore, by multiplying the number of smallest minimum values by the ratio of the effective culturing area and the area of the visual field, it is possible to calculated the total number of cells in the culture vessel 2 easily and precisely.

In this way, with the cell analysis apparatus 1 and method according to this embodiment, by smoothing the image and counting the number of smallest minimum values with the image processing unit 4, it is possible to calculate the number of cells easily and precisely without performing shape recognition of the cells A in the image. Therefore, unlike the conventional methods which take time for shape recognition, advantages are afforded in that it is possible to quickly calculate the number of cells in the culture vessel 2, and it is possible to quickly determine the cell generation cycle.

In addition, since it is not necessary to exfoliate the cells A from the culture vessel 2 for counting the number of cells in the culture vessel 2, advantages are afforded in that the stress on the cells A during culturing can be reduced, and the cells A are allowed to efficiently proliferate.

Figure 9:
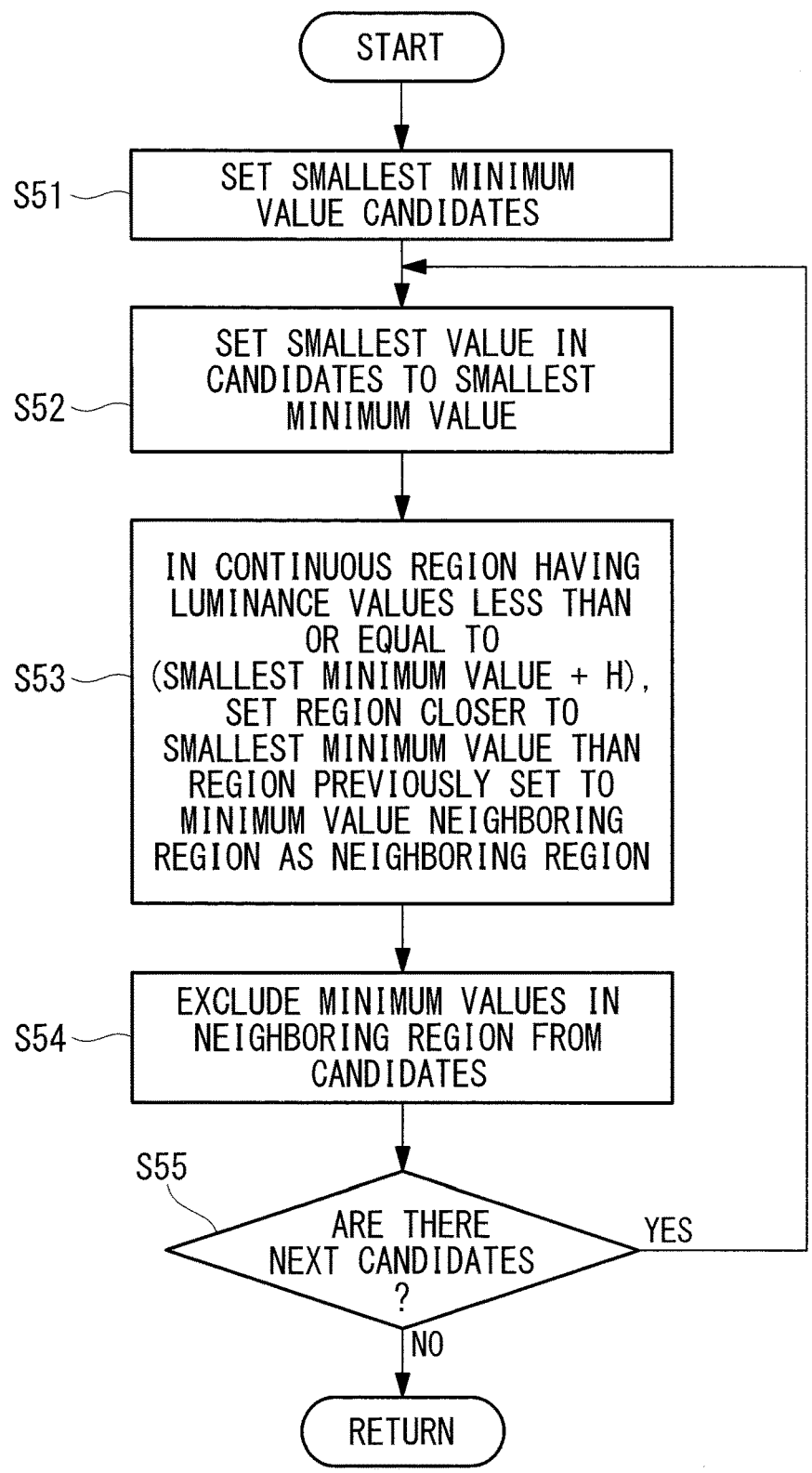
FIG. 9 is a flowchart showing an example of the smallest-minimum-value extracting step in FIG. 6.

In this embodiment, it has been assumed that the threshold value H is set, and the minimum value that is the smallest in a region containing the minimum value $P_N$ and having luminance values less than or equal to a value obtained by adding the threshold value H and this minimum value $P_N$ is extracted at the smallest minimum value. Instead of this, however, as shown in FIG. 9, the minimum values detected by the minimum-value detecting unit 8 may be set as smallest minimum value candidates, the one having the smallest luminance value among the smallest minimum value candidates may be set as the smallest minimum value, in a continuous region containing the set smallest minimum value and having luminance values less than or equal to a luminance value obtained by adding a prescribed threshold to the smallest minimum value, a region closer to the smallest minimum value than a region already set as a neighboring region may be set as a neighboring region, and all of the minimum values in this neighboring region may be excluded from the extraction targets as smallest minimum values, and these steps may be repeated until there are no more smallest minimum value candidates.

Figure 8:
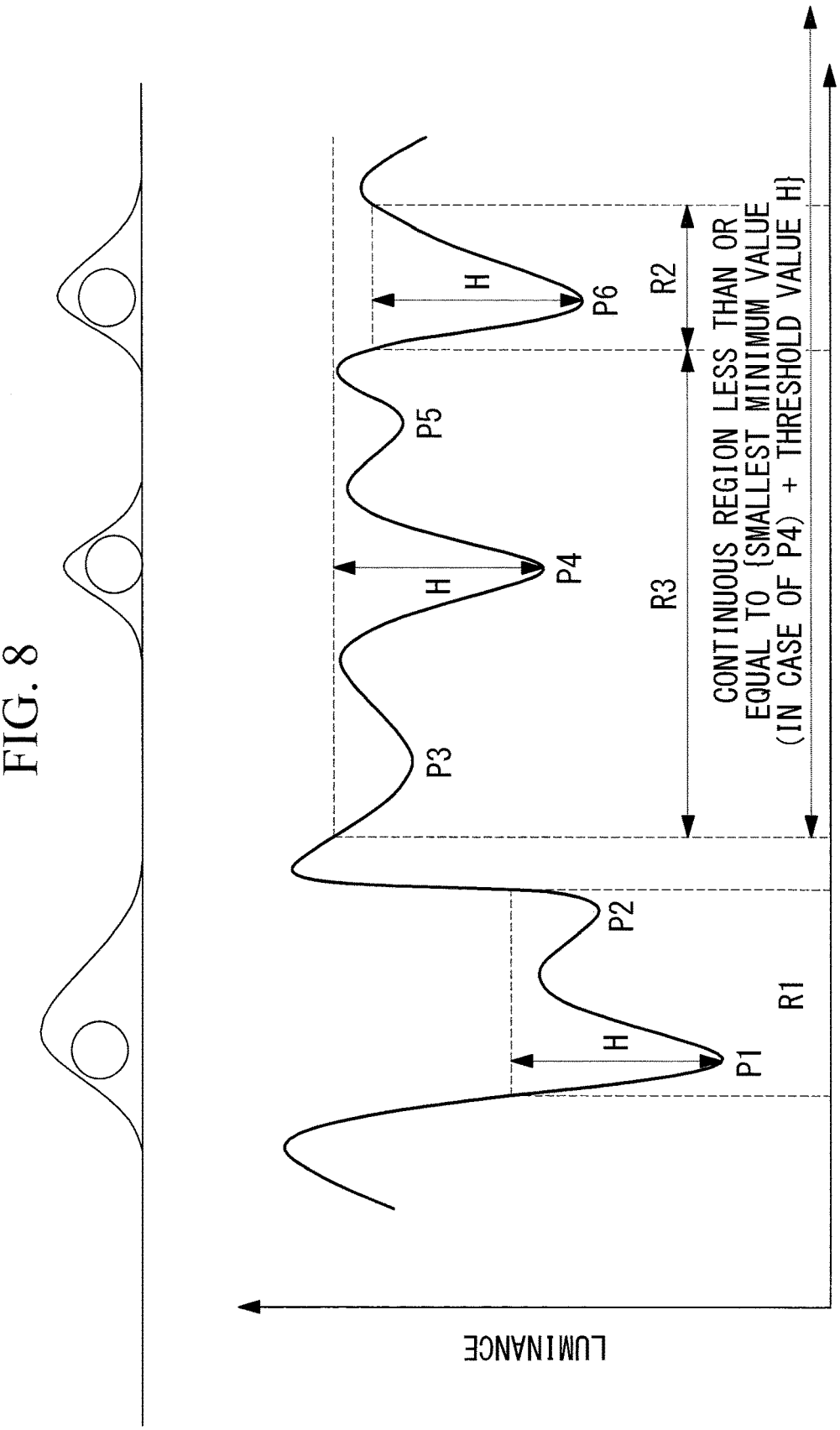
FIG. 8 is a diagram for explaining the operation of a modification of the smallest-minimum-value extracting unit in FIG. 6.

For example, as shown in FIG. 8, six minimum values are detected, and first, all of the minimum values P1 to P6 are set as smallest minimum value candidates (step S51).

At this time, the luminance values of the minimum values P1 to P6 among the candidates are, in decreasing order, P1, P6, P2, P4, P3, and P5.

Next, the minimum value that is the smallest among the candidates is set as the smallest minimum value (step S52).

In this case, the minimum value P1 is set as the initial smallest minimum value.

Then, in a continuous region containing the set smallest minimum value P1 and having luminance values less than or equal to a value obtained by adding the prescribed threshold value H to that smallest minimum value P1, a region closer to the smallest minimum value P1 than a region already set as a neighboring region of the minimum values is set as a neighboring region R1 of the smallest minimum value P1 (step S53). Here, since there is no region in which a neighboring region of the smallest minimum value has already been set, the region R1 becomes the neighboring region of the smallest minimum value P1 as it is. Accordingly, all of the minimum values P1 and P2 contained in the neighboring region R1 are excluded from the smallest minimum value candidates (step S54).

In this state, since the minimum values P3 to P6 remain in the smallest minimum value candidates, the processing from step S52 is repeated (step S55). Among these minimum values P3 to P6, the minimum value that is the smallest is the minimum value P6. Therefore, the minimum value P6 is set as the smallest minimum value (step S52), and in a continuous region containing the smallest minimum value P6 and having luminance values less than or equal to a value obtained by adding the prescribed threshold H to the luminance value of the smallest minimum value P6, a region that is closer to the smallest minimum value P6 than the region R1 already set as the neighboring region is set as a neighboring region R2 of the smallest minimum value P6 (step S53). Accordingly, the minimum value P6 contained in the neighboring region R2 is excluded from the next smallest minimum value candidates (step S54).

In this state, since the minimum values P3 to P5 remain in the next smallest minimum value candidates, the processing from step S52 is repeated, and the minimum value P4, which is the smallest among these minimum values P3 to P5, is set as the next smallest minimum value (step S52).

Then, in a continuous range containing the smallest minimum value P4 and having luminance values less than or equal to a value obtained by adding the prescribed threshold H to the luminance value of the smallest minimum value P4, a region closer to the smallest minimum value P4 than regions R1 and R2 already set as the neighboring regions is set as the neighboring region R3 (step S53). Since the minimum values P3 to P5 are contained in the neighboring region R3, these minimum values P3 to P5 are excluded from the smallest minimum value candidates (step S54), so that there are no more next candidates (step S55).

As a result, the minimum values P1, P4, and P6 are extracted as the smallest minimum values.

By doing so, as the process of extracting smallest minimum values proceeds, the number of minimum values that are smallest minimum value candidates decreases, and therefore, advantages are afforded in that it is possible to proceed with the smallest minimum value extracting process in an accelerating manner, and it is possible to more quickly calculate the number of cells.

Figure 11:
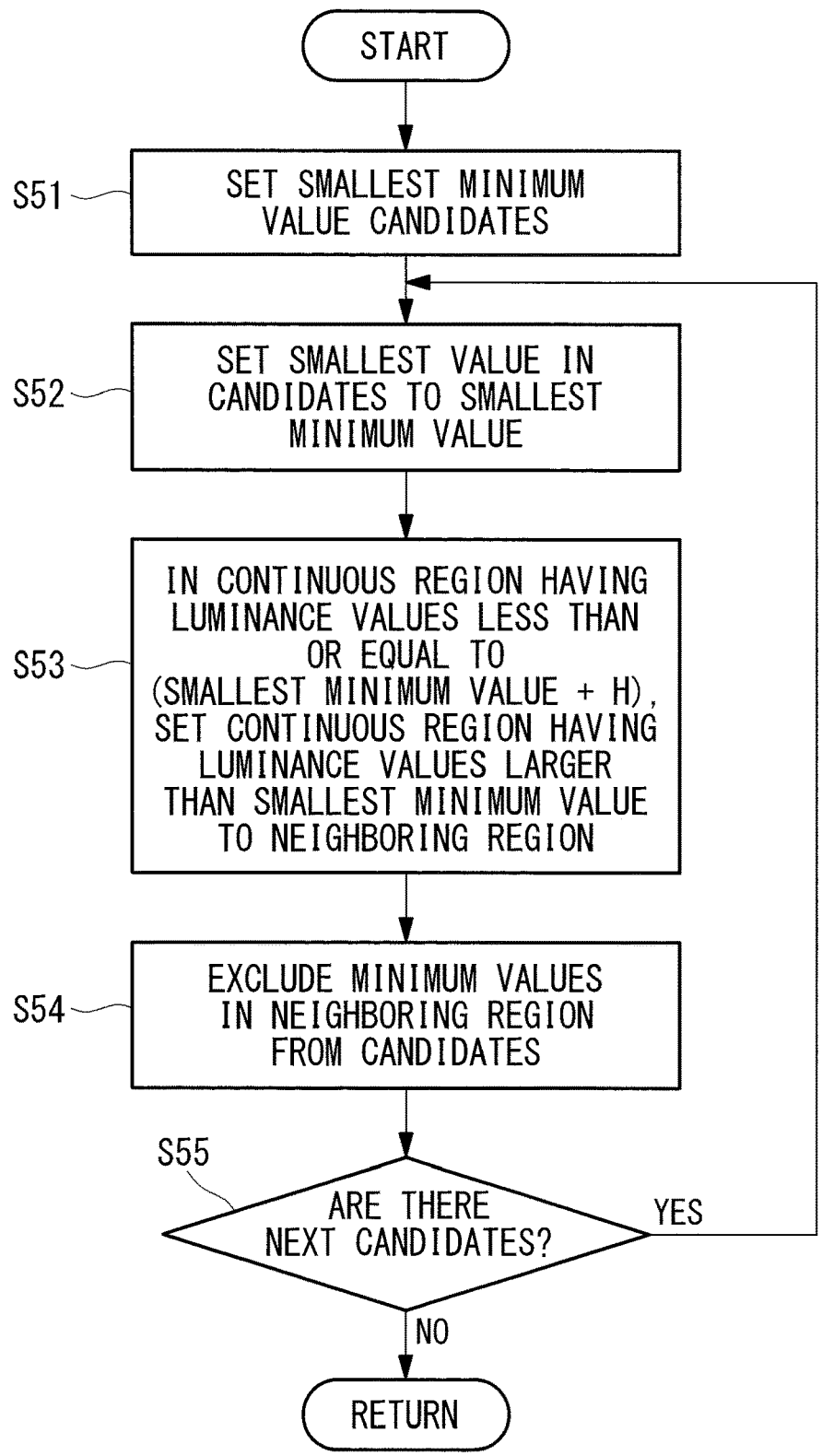
FIG. 11 is a flowchart showing another example of the smallest-minimum-value extracting step in FIG. 6.

Furthermore, as shown in FIG. 11, in a continuous region containing the smallest minimum value and having luminance values less than or equal to a value obtained by adding the prescribed threshold H to that smallest minimum value, a continuous region having luminance values larger than the smallest minimum value that is already set may be set as the neighboring region.

Figure 10:
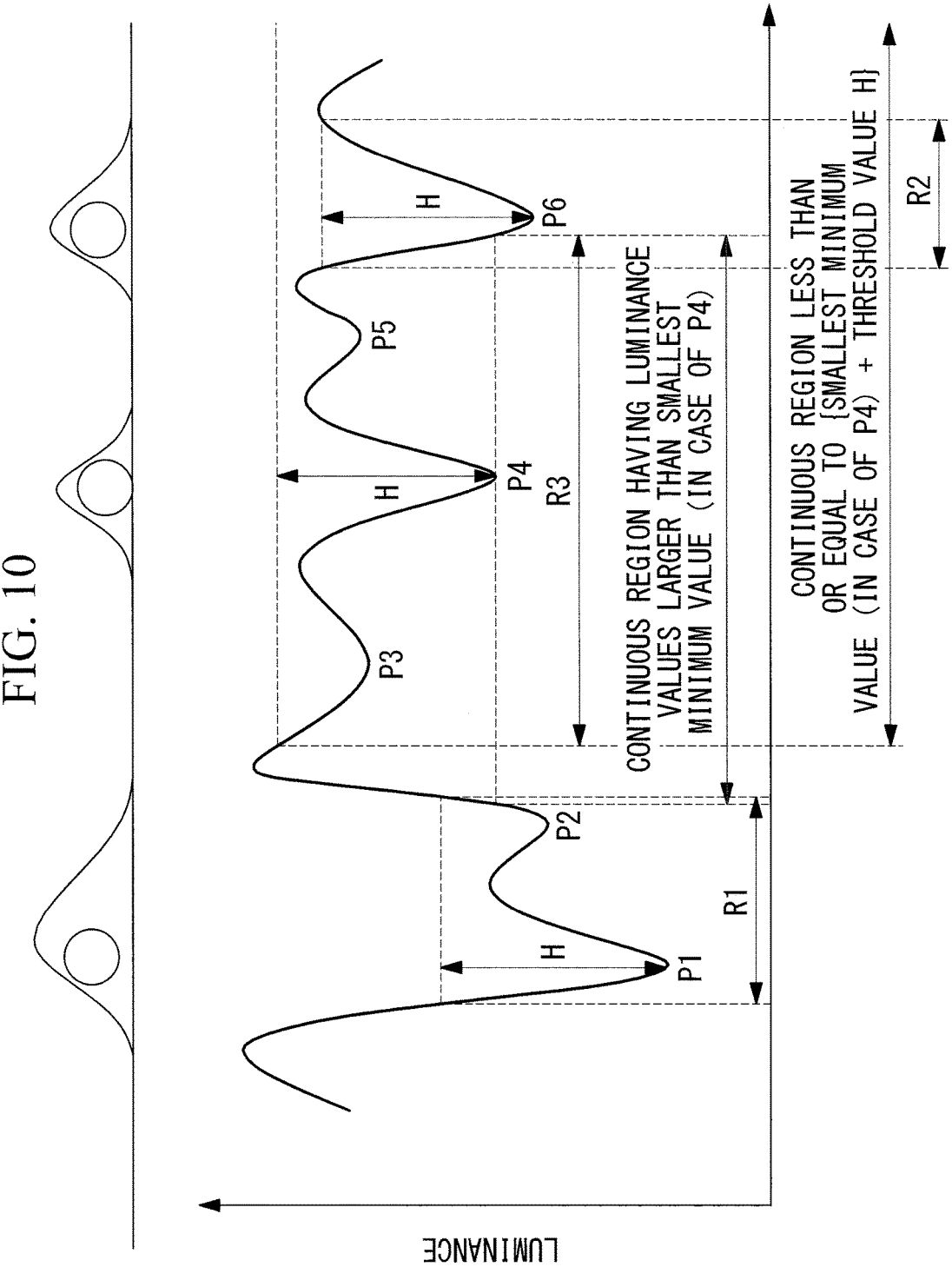
FIG. 10 is a diagram for explaining the operation of another modification of the smallest-minimum-value extracting step in FIG. 6.

For example, as shown in FIG. 10, all of the minimum values P1 to P6 are set as smallest minimum value candidates (step S51), and the minimum value that is the smallest among the candidates is set as the smallest minimum value (step S52).

In this case, the minimum value P1 is set as the initial smallest minimum value, and within a continuous region that is inside the continuous region containing the set smallest minimum value P1 and having luminance values of the smallest minimum value P1 less than or equal to a value obtained by adding the prescribed threshold value H to the smallest minimum value P1, a continuous region having luminance values larger than the smallest minimum value P1 is set as a neighboring region R1 (step S53). Accordingly, all of the minimum values P1 and P2 contained in the neighboring region R1 are excluded from the smallest minimum value candidates (step S54).

In this state, since the minimum values P3 to P6 remain in the next smallest minimum value candidates, the processing from step S52 is repeated (step S55). Then, when all of the minimum values P3 to P6 contained in a neighboring region R2 of the smallest minimum value P6 and a neighboring region R3 of the smallest minimum value P4 are excluded from the smallest minimum value candidates (step S54), so that there are no more next candidates (step S55), the minimum values P1, P4, and P6 are extracted as the smallest minimum values.

Although it has been assumed that the smallest minimum values for all regions in the image are extracted in this embodiment, instead of this, luminance value change characteristic information with which it is possible to distinguish in advance between a cell region in which the cells A exist and a background region in which the cells A do not exist may be stored, the cell region may be extracted from the acquired image on the basis of this luminance value change characteristic information (cell-region extracting step), and the processing from the minimum-value detecting unit 8 onward may be applied to the extracted cell region. In this case, the cell analysis apparatus 1 is provided with a cell-region extracting unit (not illustrated) that extracts a region in which the cells A exist in the image acquired by the cell image acquisition unit 3. By doing so, since the region to be processed is limited to the region in which the cells A exist, it is possible to speed up the processing even more.

Although it has been assumed that an image of part of the culturing surface 2a in the culture vessel 2 is acquired to calculate the number of cells in this embodiment, instead of this, a plurality of images of different locations on the culturing surface 2a may be acquired, and after the counted number of cells are averaged, the overall number of cells in the culture vessel 2 may be calculated by the cell-count calculating unit 11. By doing so, an advantage is afforded in that, even if there are variations in the distribution of cells A, it is possible to precisely calculate the number of cells in the culture vessel 2.

In addition, the cell image acquisition unit 3 may be provided with means for adjusting at least one of the illumination light level illuminating the cells A and the imaging sensitivity.

The means for adjusting the illumination light level should measure the illumination light level and adjust it to a prescribed illumination light level.

In addition, the means for adjusting the imaging sensitivity may calculate an average luminance value in the image or in a prescribed region in the image, and may adjust the imaging sensitivity so that the average luminance value becomes a prescribed value.

The imaging sensitivity may be adjusted according to the brightness of the acquired image, or it may be adjusted on the basis of the brightness of an image acquired before starting the measurement. In addition, in the case where a plurality of images are acquired to calculate the number of cells, the imaging sensitivity may be adjusted according to the brightness of each image.

In addition, in the case where a plurality of images are acquired, the number of cells may be calculated for the case where a preset number of images are acquired. Here, in the case where the number of cells are calculated for a plurality of types of culture vessels 2 having different surface areas, the number of images to be acquired may be set for each surface area of the culture vessels 2.

The number of cells in each of the acquired images may be counted, the average value of the number of cells may be calculated, and the processing from image acquisition onward may be repeated until the variation rate of the average number of cells is less than or equal to a prescribed value.

In addition, although it has been assumed in this embodiment that the cellular nuclei are extracted from a phase contrast image using the smallest minimum values, it is not necessarily limited to a phase contrast image; instead of this, in the case of a fluorescence image, for example, the cellular nuclei may be extracted using largest maximum values. In this case, the cell analysis apparatus 1 may be provided with a maximum-value detecting unit and a largest-maximum-value extracting unit instead of the minimum-value detecting unit 8 and the smallest-minimum-value extracting unit 9. In addition, in the cell analysis method using this cell analysis apparatus 1, instead of the minimum-value detecting step S3 and the smallest-minimum-value extracting step S4, a maximum-value detecting step of detecting maximum values of the luminance values using the maximum-value detecting unit and a largest-maximum-value extracting step of extracting a largest maximum value that is the largest in a region according to the sizes of the cells A using the largest-maximum-value extracting unit may be executed.

The above-described embodiment leads to the following invention.

An aspect of the present invention is a cell analysis apparatus comprising: a cell image acquisition unit that acquires an image of cells in a culture vessel in which cells are cultured; a smoothing processing unit that smooths luminance values in the image acquired by the cell image acquisition unit; a minimum-value detecting unit that detects minimum values of the luminance values smoothed by the smoothing processing unit; a smallest-minimum-value extracting unit that extracts smallest minimum values which are the smallest in regions according to the sizes of the cells, from the minimum values detected by the minimum-value detecting unit; a counting unit that counts the number of smallest minimum values extracted by the smallest-minimum-value extracting unit; and a cell-count calculating unit that calculates the number of cells in the culture vessel on the basis of the number of smallest minimum values counted by the counting unit.

According to this aspect, the luminance values in an image of the inside of the culture vessel acquired by the operation of the cell image acquisition unit are smoothed by the operation of the smoothing processing unit, whereby the luminance value peaks become gentle, and small peaks are eliminated. Therefore, small peaks are excluded from the minimum values detected in the minimum-value detecting unit, and it is possible to easily extract the smallest minimum values in the smallest-minimum-value extracting unit. Since the extracted smallest minimum values are the smallest within a regions according to the sizes of the cells, the number of smallest minimum values and the number of cells are equal, and by counting the number of smallest minimum values in the counting unit, it is possible to detect, with superior precision, the number of cells existing in the visual field of the cell image acquisition unit. Thus, it is possible to precisely calculate the number of cells in the culture vessel with the cell-count calculating unit on the basis of the number of cells in the visual field, detected in this way.

In the above-described aspect, for each of the minimum values detected by the minimum-value detecting unit, the smallest-minimum-value extracting unit may extract, as the smallest minimum value, the minimum value that is the smallest in a continuous region containing said minimum value and having luminance values less than or equal to a value obtained by adding a prescribed threshold to said minimum value.

By doing so, a continuous region having luminance values less than or equal to a value obtained by adding the prescribed threshold value to the minimum values close to the minimum value positions can be set according to the sizes of the cells, and the smallest minimum value can be easily extracted.

In the above-described aspect, the smallest-minimum-value extracting unit may repeatedly: set each of the minimum values detected by the minimum-value detecting unit as a smallest minimum value candidate; extract, as the smallest minimum value, one of the smallest minimum value candidates for which the luminance value is the smallest; set, as a neighboring region, a region that is closer to the smallest minimum value than a region already set as a neighboring region, in a continuous region containing the extracted smallest minimum value and having luminance values less than or equal to a value obtained by adding a prescribed threshold to the smallest minimum value; and exclude all of the minimum values existing in the neighboring region from the smallest minimum value candidates, until there are no more of the smallest minimum value candidates.

By doing so, when extracting the smallest minimum values, the minimum values that are cannot be smallest minimum values existing in the periphery can be excluded from the smallest minimum value candidates, and it is possible to shorten the time required for extracting the smallest minimum values.

In the above-described aspect, the smallest-minimum-value extracting unit may repeatedly: set each of the minimum values detected by the minimum-value detecting unit as a smallest minimum value candidate; extract one for which the luminance value is the smallest in the smallest minimum value candidates as the smallest minimum value; set, to a neighboring region, a continuous region having luminance values larger than the smallest minimum value that is already set, in a continuous region containing the extracted smallest minimum value and having luminance values less than or equal to a value obtained by adding a prescribed threshold to the smallest minimum value; and exclude all of the minimum values existing in the neighboring region from the smallest minimum value candidates, until there are no more of the smallest minimum value candidates.

The above-described aspect may further comprise a cell-region extracting unit that extracts a cell region in which cells exist, in the image acquired by the cell image acquisition unit, wherein the minimum-value detecting unit may detect the minimum values of the luminance values in the image, for the region in which the cells exist, extracted by the cell-region extracting unit.

By doing so, since the number of cells is counted by extracting the smallest minimum values only in a region in which the cells exist, which is extracted by the cell-region extracting unit, it is possible to calculate the number of cells more quickly.

Another aspect of the present invention is a cell analysis apparatus comprising: a cell image acquisition unit that acquires an image of cells in a culture vessel in which cells are cultured; a smoothing processing unit that smooths luminance values in the image acquired by the cell image acquisition unit; a maximum-value detecting unit that detects maximum values of the luminance values smoothed by the smoothing processing unit; a largest-maximum-value extracting unit that extracts largest maximum values which are the largest in regions according to the sizes of the cells, from the maximum values detected by the maximum-value detecting unit; a counting unit that counts the number of largest maximum values extracted by the largest-maximum-value extracting unit; and a cell-count calculating unit that calculates the number of cells in the culture vessel on the basis of the number of largest maximum values counted by the counting unit.

Another aspect of the present invention is cell analyzing method comprising: an image-capturing step of acquiring an image of cells in a culture vessel in which the cells are cultured; a smoothing step of smoothing luminance values in the image acquired in the image-capturing step; a minimum-value detecting step of detecting minimum values of the luminance values smoothed in the smoothing step; a smallest-minimum-value extracting step of extracting smallest minimum values that are the smallest in regions according to the sizes of the cells, from the minimum values detected in the minimum-value detecting step; a counting step of counting the number of the smallest minimum values extracted in the smallest-minimum-value extracting step; and a cell-count calculating step of calculating the number of cells in the culture vessel on the basis of the number of smallest minimum values counted in the counting step.

In the above-described aspect, for each of the minimum values detected in the minimum-value detecting step, the smallest-minimum-value extracting step may extract, as the smallest minimum value, the minimum value that is the smallest in a continuous region containing each of the minimum values and having luminance values less than or equal to a value obtained by adding a prescribed threshold to each of the minimum values.

In the above-described aspect, the smallest-minimum value extracting step may repeat: a step of setting each of the minimum values detected in the minimum-value extracting step as a smallest minimum value candidate; a step of extracting, as a smallest minimum value, one of the smallest minimum value candidates for which the luminance value is the smallest; a step of setting, as a neighboring region, a region closer to the smallest minimum value than a region already set as a neighboring region, in a continuous region containing the extracted smallest minimum value and having luminance values less than or equal to a value obtained by adding a prescribed threshold to the smallest minimum value; and a step of excluding all of the minimum values that exist in the neighboring region from the smallest minimum value candidates, until there are no more of the smallest minimum value candidates.

In the above-described aspect, the smallest-minimum value extracting step may repeat: a step of setting each of the minimum values detected in the minimum-value extracting step as a smallest minimum value candidate; a step of extracting, as the smallest minimum value, one of the smallest minimum value candidates for which the luminance value is the smallest; a step of setting, as a neighboring region, a continuous region having luminance values larger than the smallest minimum value that is already set, in a continuous region containing the extracted smallest minimum value and having luminance values less than or equal to a value obtained by adding a prescribed threshold to the smallest minimum value; and a step of excuding all of the minimum values that exist in the neighboring region from the smallest minimum value candidates, until there are no more of the smallest minimum value candidates.

The above-described aspect may further comprise: a cell-region extracting step of extracting a region in which cells exist, in the image acquired in the image capturing step, wherein the minimum-value detecting step may detect the minimum values of the luminance values in the image, for the region in which the cells exist, extracted in the cell-region extracting step.

Another aspect of the present invention is a cell analyzing method comprising: an image-capturing step of acquiring an image of cells in a culture vessel in which the cells are cultured; a smoothing step of smoothing luminance values in the image acquired in the image-capturing step; a maximum-value detecting step of detecting maximum values of the luminance values smoothed in the smoothing step; a largest-maximum-value extracting step of extracting largest maximum values that are the largest in regions according to the sizes of the cells, from the maximum values detected in the maximum-value detecting step; a counting step of counting the number of the largest maximum values extracted in the largest-maximum-value extracting step; and a cell-count calculating step of calculating the number of cells in the culture vessel on the basis of the number of largest maximum values counted in the counting step.

REFERENCE SIGNS LIST 1 cell analysis apparatus
2 culture vessel
3 cell image acquisition unit
7 smoothing processing unit
8 minimum-value detecting unit
9 smallest-minimum-value extracting unit
10 counting unit
11 cell-count calculating unit
S1 image-capturing step
S2 smoothing step
S3 minimum-value detecting step
S4 smallest-minimum-value extracting step
S5 counting step
S6 cell-count calculating step

The invention claimed is:

1. A cell analysis apparatus comprising a processor, the processor comprising hardware and configured to execute the steps of:
   acquiring a first image of cells in a culture vessel in which cells are cultured;
   creating a second image by smoothing luminance values in the first image;
   detecting minimum values of the luminance values from the second image;
   extracting smallest minimum values each of which is the smallest among the minimum values in a search region, wherein the search region corresponds to each of the minimum values and is defined according to the sizes of the cells;
   counting a number of the smallest minimum values; and
   calculating the number of cells in the culture vessel on the basis of the number of the smallest minimum values.

2. A cell analysis apparatus according to claim 1, wherein the search region is defined as a continuous region containing said minimum value and having luminance values less than or equal to a value obtained by adding a prescribed threshold to said minimum value.

3. A cell analysis apparatus according to claim 2, wherein the processor executes the step of extracting the smallest minimum values by repeatedly:
   setting each of the minimum values a smallest minimum value candidate;
   extracting, as the smallest minimum value, one of the smallest minimum value candidates for which the luminance value is the smallest;
   setting, as a neighboring region, a region that is closer to the smallest minimum value than a region already set as a neighboring region, in the search region; and
   excluding all of the minimum values existing in the neighboring region from the smallest minimum value candidates, until there are no more of the smallest minimum value candidates.

4. A cell analysis apparatus according to claim 2, wherein the processor executes the step of extracting the smallest minimum values by repeatedly:
   setting each of the minimum values as a smallest minimum value candidate;
   extracting one for which the luminance value is the smallest in the smallest minimum value candidates as the smallest minimum value;
   setting, to a neighboring region, a continuous region having luminance values larger than the smallest minimum value that is already set, in the search region; and
   excluding all of the minimum values existing in the neighboring region from the smallest minimum value candidates, until there are no more of the smallest minimum value candidates.

5. A cell analysis apparatus according to claim 1, wherein the processor is configured to further execute a step of:
   extracting a cell region in which cells exist, in the first image, and wherein the minimum values of the luminance values in the second image are detected in the cell region.

6. A cell analysis apparatus comprising a processor, the processor comprising hardware and configured to execute the steps of:
   acquiring a first image of cells in a culture vessel in which cells are cultured;
   creating a second image by smoothing luminance values in the first image;
   detecting maximum values of the luminance values from the second image;
   extracting largest maximum values each of which is the largest among the maximum values in a search region, wherein the search region corresponds to each of the maximum values and is defined according to the sizes of the cells;
   counting a number of the largest maximum values; and
   calculating the number of cells in the culture vessel on the basis of the number of the largest maximum values.

7. A cell analyzing method comprising:
   an image-capturing step of acquiring a first image of cells in a culture vessel in which the cells are cultured;
   a creating a second image step by smoothing luminance values in the first image;
   a detecting step of detecting minimum values of the luminance values from the second image;
   an extracting step of extracting smallest minimum values each of which is the smallest among the minimum values in a search region, wherein the search region corresponds to each of the minimum values and is defined according to the sizes of the cells;
   a counting step of counting a number of the smallest values; and
   a cell-count calculating step of calculating the number of cells in the culture vessel on the basis of the number of the smallest minimum values.

8. A cell analysis method according to claim 7, wherein the search region is defined as a continuous region containing each of the minimum values and having luminance values less than or equal to a value obtained by adding a prescribed threshold to each of the minimum values.

9. A cell analysis method according to claim 8, wherein the extracting step repeats:
   a step of setting each of the minimum values a smallest minimum value candidate;
   a step of extracting, as a smallest minimum value, one of the smallest minimum value candidates for which the luminance value is the smallest;
   a step of setting, as a neighboring region, a region closer to the smallest minimum value than a region already set as a neighboring region, in the search region; and
   a step of excluding all of the minimum values that exist in the neighboring region from the smallest minimum value candidates, until there are no more of the smallest minimum value candidates.

10. A cell analysis method according to claim 8, wherein the extracting step repeats:
    a step of setting each of the minimum values as a smallest minimum value candidate;
    a step of extracting, as the smallest minimum value, one of the smallest minimum value candidates for which the luminance value is the smallest;
    a step of setting, as a neighboring region, a continuous region having luminance values larger than the smallest minimum value that is already set, in the search region; and
    a step of excluding all of the minimum values that exist in the neighboring region from the smallest minimum value candidates, until there are no more of the smallest minimum value candidates.

11. A cell analysis method according to claim 7, further comprising:
    a cell-region extracting step of extracting a region in which cells exist, in the first image, and
    wherein the minimum values of the luminance values in the second image are detected in the cell region.

12. A cell analyzing method comprising:
    an image-capturing step of acquiring a first image of cells in a culture vessel in which the cells are cultured;
    a creating a second image step by smoothing luminance values in the first image;
    a detecting step of detecting maximum values of the luminance values from the second;
    an extracting step of extracting largest maximum values each of which is the largest among the maximum values in a search region, wherein the search region corresponds to the maximum values and is defined according to the sizes of the cells;
    a counting step of counting a number of the largest maximum values; and
    a cell-count calculating step of calculating the number of cells in the culture vessel on the basis of the number of the largest maximum values.

* * * * *